United States Patent [19]
Kurosaki et al.

[11] Patent Number: 4,587,063
[45] Date of Patent: May 6, 1986

[54] PROCESS FOR THE PREPARATION OF PHOSPHORIC DIESTERS

[75] Inventors: Tomihiro Kurosaki, Oosaka; Norio Nishikawa, Wakayama, both of Japan

[73] Assignee: KAO Corporation, Tokyo, Japan

[21] Appl. No.: 511,948

[22] Filed: Jul. 8, 1983

[30] Foreign Application Priority Data

Jul. 15, 1982 [JP] Japan ................. 57-123280

[51] Int. Cl.$^4$ ............................................. C07F 9/09
[52] U.S. Cl. .................................... 556/146; 558/114
[58] Field of Search ............................. 260/990, 980

[56] References Cited
FOREIGN PATENT DOCUMENTS
2123424 2/1984 United Kingdom ............... 260/990

OTHER PUBLICATIONS
Kosolapofd, "Organophosphorus Compounds", (1950), p. 233.

Primary Examiner—Anton H. Sutto
Attorney, Agent, or Firm—Oblon, Fisher, Spivak, McClelland & Maier

[57] ABSTRACT

An industrially advantageous process of preparing phosphoric acid diesters of high purity.

To a mixture of phosphoric esters comprising phosphoric monoesters and phosphoric diesters, a base is added in an amount of 0.5–1.3 equivalents based on phosphorus atoms which are contained in the mixture. The phosphoric monoesters are converted into orthophosphoric acid and organic hydroxyl compounds by hydrolysis, after which step the orthophosphoric acid and organic hydroxyl compounds are removed from the mixture.

5 Claims, No Drawings

PROCESS FOR THE PREPARATION OF PHOSPHORIC DIESTERS

BACKGROUND OF THE INVENTION (i) Field of the Invention

This invention relates to a process for the preparation of phosphoric diesters of high purity and more particularly, to a process for preparing phosphoric diesters of high purity by selectively hydrolyzing phosphoric monoesters in phosphoric ester mixtures comprising phosphoric monoesters and phosphoric diesters, and removing the resulting hydrolyzates from the mixtures.

(ii) Description of the Prior Art

Phosphoric esters of organic hydroxyl compounds are utilized as a detergent, emulsifier, antistatic agent, oil for fibers, and the like. In these applications, phosphoric diesters are frequently employed as mixtures with phosphoric monoesters, phosphoric triesters or condensed phosphoric esters.

On the other hand, highly pure phosphoric diester such as, for example, di-2-ethylhexyl phosphate, is an important compound which has been widely used as a liquid ion exchanger (solvent for metal extraction) in the fields of refining of uranium ores, recovery of uranium from phosphoric acid obtained by a wet process, refining of nickel, cobalt, rare earth elements, and the like, or recovery of valuable metals from waste liquors discharged from surface treatments of metallic materials.

Phosphoric esters of organic hydroxyl compounds are industrially produced by reaction of phosphorylating agents such as phosphorus oxychloride, phosphorus pentaoxide, polyphosphoric acid, and the like with organic hydroxyl compounds. For the production of phosphoric diesters, it is usual to use phosphorus oxychloride. When phosphorus pentaoxide is used as a phosphorylating agent, a so-called sesquiphosphate (comprising a mixture of almost equimolar amounts of phosphoric diester and phosphoric monoester along with condensed phosphoric esters) is obtained. With polyphosphoric acids, phosphoric diesters are not substantially produced.

In general, the reaction between organic hydroxyl compounds and phosphorus oxychloride for the production of phosphoric diesters is complicated. Products obtained by ordinary production processes usually contain impurities such as phosphoric monoesters and phosphoric triesters, and the purity of phosphoric diester is at most as low as 70–80%.

In order to obtain highly pure phosphoric diesters, purification is necessary. This is ordinarily effected by utilizing a difference in the physical property such as, for example, solubility between a phosphoric diester and impurities such as a phosphoric monoester. However, for example in the purification by extraction of di-2-ethylhexyl phosphate, phase separation becomes very poor because only a small amount of mono-2-ethylhexyl phosphate is present as an impurity. This will produce a great trouble for the purification on an industrial scale.

SUMMARY OF THE INVENTION

Under these circumstances, we have made intersive studies to develop a process for preparing highly pure phosphoric diesters in an industrially advantageous manner. As a result, it was unexpectedly found that although phosphoric esters of higher alcohols were considered to have a tendency of hydrolysis in the order of triester, diester and monoester, mono anions of phosphoric monoesters were much more likely to hydrolyze under specific hydrolysis conditions, i.e. in a weakly acidic or weakly alkaline region, with anions of phosphoric diesters undergoing little or no hydrolysis.

According to the present invention, there is provided a process for the preparation of phosphoric diesters characterized by adding, to a mixture of phosphoric esters comprising phosphoric monoesters and phosphoric diesters, a base in an amount of 0.5–1.3 equivalents based on phosphorus atoms contained in the mixture thereby converting by hydrolysis the phosphoric monoesters into orthophosphoric acid and organic hydroxyl compounds, and removing the orthophosphoric acid and organic hydroxyl compounds from the mixture.

DETAILED DESCRIPTION OF THE INVENTION AND PREFERRED EMBODIMENTS

The phosphoric ester mixtures used in the process of the invention may be mixtures derived from any sources provided that they comprise monoesters and diesters. For instance, reaction products obtained by reaction between hydroxyl compounds and phosphorus pentaoxide, phosphorus oxychloride, or orthophosphoric acid are preferably used. It will be noted that the reaction between hydroxyl compounds and phosphorus oxychloride involve side production of hydrogen chloride as will be described hereinafter, so that it is necessary to add, aside from 0.5–1.3 equivalents of a base, an additional base for neutralizing the hydrogen chloride.

The organic hydroxyl compounds include, for example, ethyl alcohol, propyl alcohol, butyl alcohol, pentyl alcohol, hexyl alcohol, 2-ethylhexyl alcohol, heptyl alcohol, octyl alcohol, nonyl alcohol, decyl alcohol, undecyl alcohol, dodecyl alcohol, tridecyl alcohol, tetradecyl alcohol, pentadecyl alcohol, hexadecyl alcohol, heptadecyl alcohol, octadecyl alcohol, oleyl alcohol, elaidyl alcohol, eicosyl alcohol, isostearyl alcohol, or linear or branched, saturated or unsaturated alcohols having 2–24 carbon atoms such as higher alcohols obtained by an oxo process, the Ziegler process, or the Guerbet process or alkylene oxide adducts ($P \leq 50$) thereof, or phenol or alkyl penhnols such as butylphenol, octylphenol, nonylphenol, dodecylphenol, etc. or their alkylene oxide addusts ($P \leq 50$), and the like.

The bases useful in the present invention may be any bases which react with phosphoric esters to form salts of phosphoric esters. Examples of the bases include alkali metal or alkaline earth metal hydroxides, carbonates and bicarbonates such as sodium hydroxide, potassium hydroxide, magnesium hydroxide, calcium hydroxide, sodium carbonate, sodium bicarbonate, magnesium carbonate, calcium carbonate, and the like, amines such as mono-, di- and tri-methylamine, mono-, di- and tri-propylamine, mono-, di- and tri-butylamine, mono-, di- and tri-octylamine, or pyridine and aniline; and alkanolamines such as mono-, di- and tri-ethanolamine, mono-, di- and tri-isopropanolamine, and the like. These bases are generally used in an amount of 0.5–1.3 equivalents based on phosphorus atoms contained in the phosphoric ester mixture.

The hydrolysis is effected at temperatures over 100° C. and particularly in the range of 130°–200° C. in order to cause the reaction to proceed smoothly. The reaction time may vary depending on the temperature and is sufficient within a range of 6–8 hour at temperatures of 140°–160° C.

Under these conditions phosphoric diesters are not hydrolyzed but phosphoric monoesters alone are hydrolyzed and converted into orthophosphoric acid and organic hydroxyl compounds. If phosphoric triesters are contained in the mixture, they are also converted into phosphoric diesters and organic hydroxyl compounds by the above treatment. Accordingly, the resulting reaction product is a mixture of salts of phosphoric diesters and orthophosphoric acid and organic hydroxyl compounds. These three types of compounds are different in chemical structure from one another and can readily be isolated and purified by the use of the difference.

In order to obtain phosphoric diesters from the mixture, orthophosphoric acid and organic hydroxyl compounds are removed by known isolation techniques such as, for example, extraction, distillation, recrystallization, ion exchange, and the like. This is industrially advantageous because organic hydroxyl compounds and phosphoric acid (as a salt) can be recovered and utilized.

In the process of the invention, phosphoric ester mixtures comprising phosphoric monoesters and phosphoric diesters should preferably be those which are obtained by reaction between organic hydroxyl compounds and phosphorus oxychloride in view of the fact that phosphoric diesters are contained in large amounts. However, this process involves side production of hydrogen chloride in large amounts during the course of the reaction (3 moles of hydrogen chloride secondarily produced per mole of phosphorus oxychloride), presenting a problem in removal of the side product and also in corrosion of reactor. Thus, this process is not necessarily favorable from the industrial viewpoint.

Industrially, reaction products which are obtained by reaction between organic hydroxyl compounds and phosphorus pentaoxide are preferably used. That is, a phosphoric ester mixture can be obtained by gradually charging 1 mole of phosphorus pentaoxide into 2–4 moles, preferably 2.9–3.1 moles, of an organic hydroxyl compound while violently agitating at a temperature ranging from a melting point of the organic hydroxyl compound to 100° C., preferably below 90° C. This phosphoric ester mixture usually comprises a phosphoric diester, phosphoric monoester, and condensed phosphoric esters (such as dialkyl pyrophosphate and the like), but contains substantially no phosphoric triester.

Although this phosphoric ester mixture may be used as a starting material for the process of the present invention, it is preferable to add water to the reaction mixture so that the condensed phosphoric esters are hydrolyzed in the acidic state for conversion into orthophosphoric esters (such as phosphoric monoester, phosphoric diester).

Accordingly, in accordance with the most preferable embodiment of the invention, there is provided a process for the preparation of phosphoric diesters which is characterized by adding water to a reaction mixture obtained by reaction between phosphorus pentaoxide and an organic hydroxyl compound so as to hydrolyze the mixture in the acidic state, further adding the resulting product a base in an amount of 1.0–2.6 moles per mole of the phosphorus pentaoxide thereby converting the phosphoric monoester into orthophosphoric acid and an organic hydroxyl compound by hydrolysis, and removing the orthophosphoric acid and organic hydroxyl compound from the mixture.

In the above embodiment, the hydrolysis in the acidic state is preferably effected at a temperature of 50°–100° C. for a time of 0.5–12 hours. During the hydrolysis, there occurs only conversion of the condensed phosphoric esters into orthophosphoric esters without hydrolysis of the phosphoric monoester and diester.

Thus, the process of the invention can provide highly pure phosphoric diesters by a very simple procedure.

The present invention is illustrated by way of examples.

EXAMPLE 1

To 390 g (3.0 moles) of 2-ethylhexanol which had been charged into a pressure-resistant vessel equipped with a thermometer, a pressure gauge, an agitator, and a bottom discharge port was added 142 g (1.0 mole) of phosphorus pentaoxide under violent agitation while maintaining the temperature at 70°–80° C., followed by reaction at 80°–90° C. for 8 hours. To the reaction product was added 53.2 g of ion-exchanged water, followed by hydrolysis at 90° C. for 3 hours under acidic conditions.

Thereafter, 420 g of an aqueous 20% sodium hydroxide solution (2.1 moles as NaOH) was added for neutralization, after which the system was closed for hydrolysis at 140°–160° C. for 7 hours. After cooling down to 60° C., the reaction solution was allowed to stand at 50°–60° C. for a time. The solution separated into two phases. The lower phase was removed, and 980 g of an aqueous 20% sulfuric acid solution (2.0 moles as $H_2SO_4$) was added to the residue, followed by violent agitation. After being allowed to stand, the lower phase was removed and the upper layer was washed three times with each 1000 g of ion-exchanged water, followed by distillation under vacuum to distil off 2-ethylhexanol, thereby obtaining 271 g of di-2-ethylhexyl phosphate having a purity as high as 99.2%.

EXAMPLE 2

222 g (3.0 moles) of n-butyl alcohol and 142 g (1.0 mole) of phosphorus pentaoxide were reacted with each other in the same manner as in Example 1, followed by addition of 36.4 g of ion-exchanged water for hydrolysis under acidic conditions.

Then, 364 g of ion-exchanged water and 389 g (2.1 moles) of tri-n-butylamine were added for neutralization, followed by hydrolysis. Thereafter, the procedure of Example 1 was repeated to obtain 149 g of di-n-butyl phosphate having a purity as high as 99.5%.

EXAMPLE 3

559 g (3 moles) of n-dodecyl alcohol and 142 g (1.0 mole) of phosphorus pentaoxide were reacted with each other in the same manner as in Example 1, after which 70.1 g of ion-exchanged water was added for hydrolysis under acidic conditions.

Further, 589 g of an aqueous 20% potassium hydroxide solution (2.1 moles as KOH) was added for neutralization, followed by hydrolysis.

In the same manner as in Example 1, the resultant lower phase was removed, after which an upper phase which had been obtained by washing with an aqueous 20% sulfuric acid solution and water was subjected to purification by recrystallization, thereby obtaining 295 g of di-n-dodecyl phosphate having a purity as high as 98.5%.

EXAMPLE 4

In the same manner as in Example 1, 811 g (3.0 moles) of n-octadodecyl alcohol and 142 g (1.0 mole) of phosphorus pentaoxide were reacted with each other, to which was added 95.3 g of ion-exchanged water for hydrolysis under acidic conditions.

Then, the reaction solution was neutralized by addition of 1180 g of an aqueous 10% potassium hydroxide solution (2.1 moles as KOH) and hydrolyzed. After cooling down to 60° C., 2000 g of an aqueous 20% sulfuric acid solution (4.08 moles as $H_2SO_4$) and 1000 g of n-hexane were added and the mixture was vigorously agitated. After being allowed to stand, the lower phase was removed, followed by washing with water, after which a residue obtained distilling off the n-hexane was purified by recrystallization with ethanol, thereby obtaining 381 g of di-n-octadecyl phosphate having a purity as high as 96.3%.

Referential Example

Into a pressure-resistant reaction vessel as used in Example 1 was charged 200 g of a phosphoric ester mixture of 55 parts of di-n-butyl phosphate, 100 parts of tri-n-butyl phosphate, and 45 parts of n-butyl alcohol [di-product (M.W.=210.2) 0.262 mole, tri-product (M.W.=266.3) 0.376 mole, total amount of di- and tri-products =0,638 mole], to which 255 g (NaOH: 1.275 moles) of an aqueous 20% sodium hydroxide solution was added for neutralization. Thereafter, the reaction system was closed and hydrolyzed at 150°-160° C. for 7 hours. After cooling to 60° C., 625 g of an aqueous 40% sulfuric acid solution (2.55 moles as $H_2SO_4$) was added, followed by violent agitation. After being allowed to stand, the lower phase was removed and the remaining upper phase was washed three times with each 500 g of ion-exchanged water, followed by distillation under vacuum to distil off the n-butyl alcohol, thereby obtaining 121 g of di-n-butyl phosphate having a purity as high as 98.7%.

EXAMPLE 5

In the same manner as in Example 1, 95.5 g (0.3 mole) of an adduct of n-dodecyl alcohol with 3 moles of ethylene oxide and 14.2 g (0.1 mole ) of phosphorus pentaoxide were reacted with each other, after which 11.0 g of ion-exchanged water was added to effect hydrolysis under acidic conditions.

Thereafter, 40.0 g of an aqueous 20% sodium hydroxide solution (0.2 moles as NaOH) was added for neutralization, followed by hydrolysis. After cooling to room temperature, 500 ml of 1N hydrochloric acid was added, to which was further added 500 ml of ethyl ether, followed by violent agitation. After being allowed to stand, the lower phase was removed and the ethyl ether was then distilled off. The resulting residue was passed through an anionic exchange resin (OH⁻form) column using 50% ethanol-water as a solvent thereby removing nonionic components by elution. Thereafter, anionic components adsorbed on the resin were eluted with 2N hydrochloric acid. This eluate was extracted with ethyl ether, followed by removing the ethyl ether by distillation and drying under reduced pressure to obtain 45.3 g of a diester of the adduct of n-dodecyl alcohol with 3 moles of ethylene oxide having a purity as high as 97.3%.

EXAMPLES 6-14

In the same manner as in Example 1, 390 parts of n-octyl alcohol was phosphorylated with 142 parts of phosphorus pentaoxide, to which was added 55 parts of ion-exchanged water for hydrolysis at 90° C. for 3 hours under acidic conditions. As a result, there was obtained a phosphoric ester mixture of the diester and monoester which was substantially free of any phosphoric triester and condensed phosphoric ester.

To 100 parts of this phosphoric ester mixture were added for neutralization a parts of an aqueous 40% sodium hydroxide solution and (100−a) parts of ion-exchanged water, after which the system was sealed and hydrolyzed at 145° C. for 7 hours. After cooling down to room temperature, 5a parts of 40% sulfuric acid was added and agitated, followed by extraction with 500 parts of ethyl ether. The ethyl ether was distilled off and the resulting extract was analyzed by the potentiometric titration method to determine hydrolysis rates of the phosphoric diester and monoester and a ratio of the diester and monoester in the extract. The results are shown in Table 1 below.

TABLE 1

| Example No. | Degree of Neutralization* | Amount of 40% NaOH a (parts) | Hydrolysis Rate of Monoester (%) | Hydrolysis Rate of Diester (%) | Ratio of Hydrolyzed Esters** (mole %) |
|---|---|---|---|---|---|
| 6 | 0 | 0 | 29.0 | 45.0 | 38.0 |
| 7 | 0.25 | 8.52 | 59.5 | 13.5 | 62.5 |
| 8 | 0.50 | 17.0 | 85.5 | 1.0 | 84.0 |
| 9 | 0.75 | 25.6 | 100.0 | 0.0 | 100.0 |
| 10 | 1.00 | 34.1 | 100.0 | 0.0 | 100.0 |
| 11 | 1.25 | 42.6 | 100.0 | 0.0 | 100.0 |
| 12 | 1.50 | 51.1 | 0.0 | 0.0 | 44.5 |
| 13 | 1.75 | 59.6 | 0.0 | 5.5 | 41.0 |
| 14 | 2.00 | 68.1 | 0.0 | 9.5 | 40.5 |

*Definition of degree of neutralization
Degree of Neutralization = $\frac{\text{Number of Moles of NaOH used for neutralization of phosphoric ester mixture}}{\text{Number of moles of total phosphorus atoms in neutralized phosphoric ester mixture}}$

**Ratio of hydrolyzed esters
Ester Ratio = $\frac{\text{Diester}}{\text{Diester + Monoester}} \times 100$ (mole %)

What is claimed is:

1. A process for the preparation of diesters characterized by adding, to a mixture of phosphoric esters comprising phosphoric monoesters and phosphoric diesters, a base in an amount of 0.5–1.3 equivalents based on phosphorus atoms contained in the mixture at a temperature of 100°–200° C., thereby converting the phosphoric monoesters into orthophosphoric acid and organic hydroxyl compounds by hydrolysis, and removing the orthophosphoric acid and organic hydroxyl compounds from the mixture.

2. A process for the preparation of phosphoric diesters characterized by adding water to a reaction mixture obtained by reaction between phosphorus pentaoxide and an organic hydroxyl compound so as to cause the mixture to be hydrolyzed in the acidic state, further adding to the resulting product a base in an amount of 1.0–2.6 moles per mole of the phosphorus pentaoxide at a temperature of 100°–200° C., thereby converting the phosphoric monoester into orthophosphoric acid and an organic hydroxyl compound by hydrolysis, and removing the orthophosphoric acid and organic hydroxyl compound from the mixture.

3. The process of claim 1 wherein the mixture of phosphoric esters comprising phosphoric monoesters and phosphoric diesters is obtained by reaction between phosphorus oxychloride and organic hydroxyl compounds.

4. The process of claim 1 wherein the mixture of phosphoric esters comprising phosphoric monoesters and phosphoric diesters is obtained by reaction between phosphorus pentaoxide and organic hydroxyl compounds.

5. The process of claim 1 wherein the mixture of phosphoric esters comprising phosphoric monoesters and phosphoric diesters is obtained by reaction between phosphorus pentaoxide and organic hydroxyl compounds, and water is added to the reaction mixture so as to cause the mixture to be hydrolyzed in the acidic state.

* * * * *